US00PP33174P2

(12) United States Plant Patent
Horvath

(10) Patent No.: US PP33,174 P2
(45) Date of Patent: Jun. 15, 2021

(54) ***SEDUM SEXANGULARE* PLANT NAMED 'YELLOWSTONE'**

(50) Latin Name: *Sedum sexangulare*
Varietal Denomination: Yellowstone

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 16/974,193

(22) Filed: Nov. 10, 2020

(51) Int. Cl.
*A01H 5/12* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 6/328
See application file for complete search history.

(56) References Cited

PUBLICATIONS

Trademark, "Yellowstone", U.S. Appl. No. 76/361,727, filed Jan. 23, 2002.*

* cited by examiner

*Primary Examiner* — Anne Marie Grunberg

(57) ABSTRACT

A new, distinct *Sedum sexangulare* plant as illustrated and described, characterized by larger foliage and golden yellow foliage color in early summer, compared to the smaller chartreuse foliage in early summer of the parent plant.

1 Drawing Sheet

Latin name: *Sedum sexangulare.*
Cultivar name: 'Yellowstone'.

BACKGROUND OF THE INVENTION

The present invention relates to a new and distinct plant of *Sedum sexangulare* plant named 'Yellowstone' characterized by larger foliage and golden yellow foliage color in early summer, compared to the smaller chartreuse foliage in early summer of the parent plant. The new *Sedum sexangulare* was raised as an open pollinated seedling, of *Sedum sexangulare* 'Golddigger', not patented, in Hebron, Ill. in 2016. The selection of the new plant was due to its' larger foliage and golden yellow foliage in early summer, compared to the smaller chartreuse foliage in early summer of the parent plant. Initial asexual reproduction has taken place at a nursery in Hebron, Ill. since 2017 by means of division, and vegetative cuttings. The new *Sedum sexangulare* has shown to be stable and identical in reproduction after rooting over 1000 plants from 2017 to 2020. No plants of the new *Sedum sexangulare* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Sedum sexangulare* plant named 'Yellowstone' characterized by larger foliage and golden yellow foliage, RHS color 1 B and C in early summer, compared to the smaller chartreuse foliage in spring of the parent plant have been observed to be unique and stable.

Plants of the new *Sedum sexangulare* plant named 'Yellowstone' can be compared to plants of, the parent *Sedum sexangulare* plant named 'Goldddiger' not patented. 1. The new *Sedum sexangulare* plant has larger foliage and golden yellow foliage, RHS color 1 B and C in early summer while the parent plant has smaller chartreuse foliage in early summer.

Plants of the new *Sedum sexangulare* can be compared to *Sedum sexangulare* 'Weisse Tatra', not patented. The new *Sedum sexangulare* plant has larger golden yellow foliage RHS color 1B and C in early summer while 'Weisse Tatra' has a green foliage all year long.

Plants of the new *Sedum sexangulare* can also be compared to *Sedum rupestre* 'Angelina', not patented. 1. The new *Sedum sexangulare* plant has smaller golden yellow foliage RHS color 1 B and C while *Sedum rupestre* 'Angelina' has large golden foliage.

DESCRIPTION OF PHOTOGRAPHS

Figure 1:
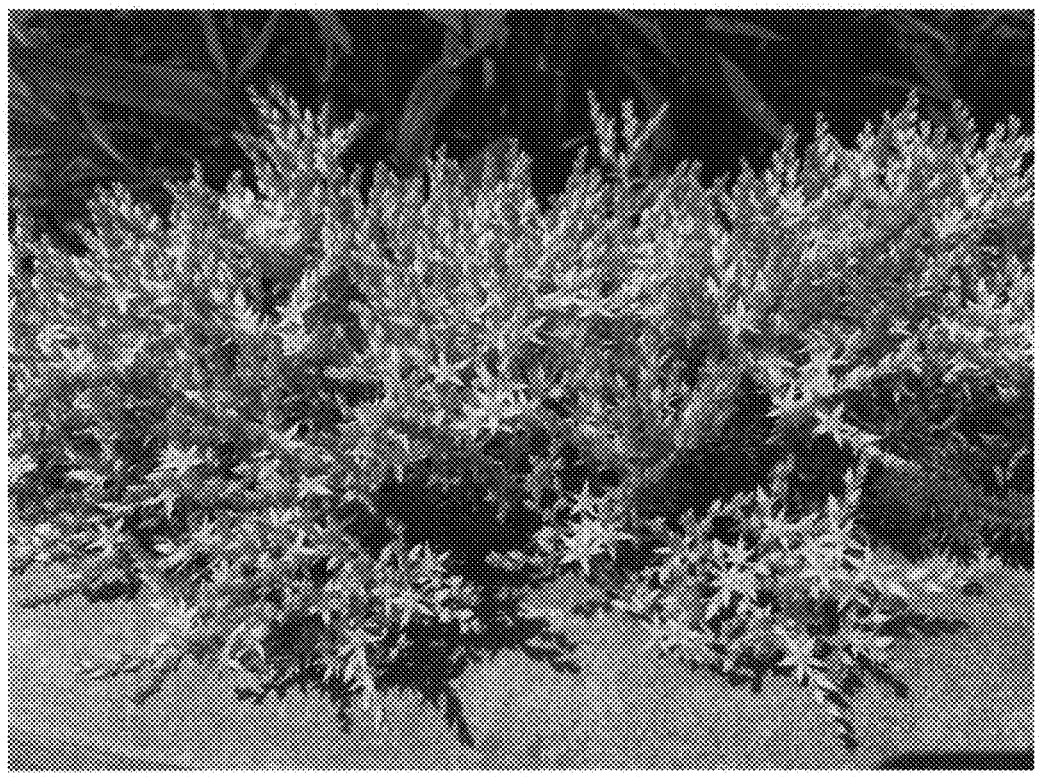
Figure 2:
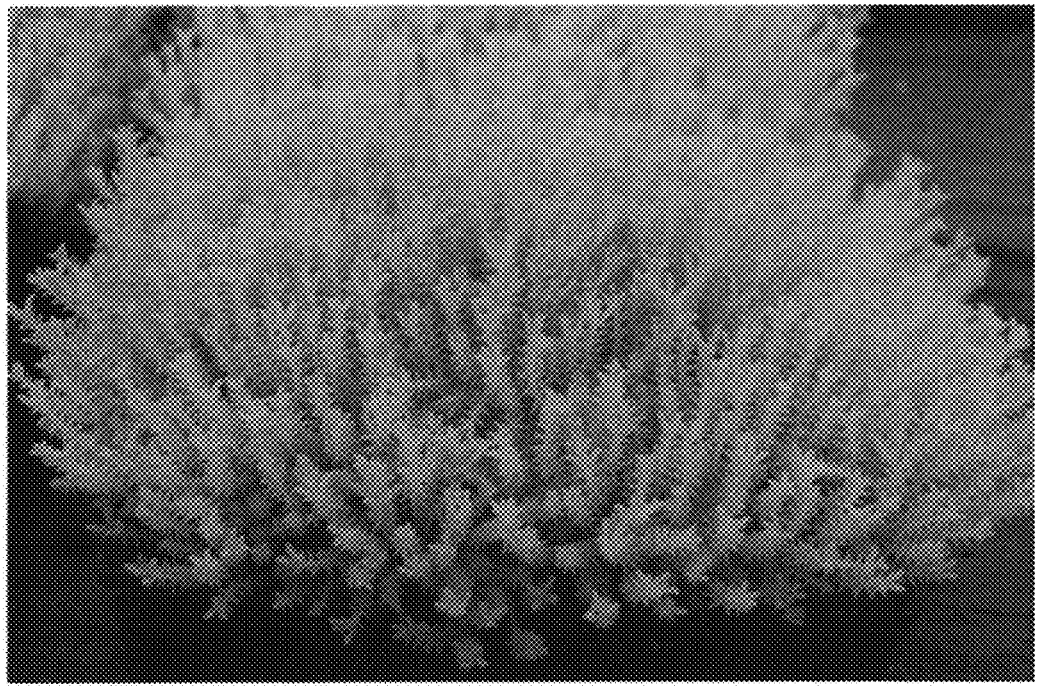

Plants pictured in the drawing were grown for one year.
FIG. 1. Close up of a flowering plant in July.
FIG. 2. A picture of container plants in June.

DETAILED BOTANICAL DESCRIPTION

In the following description, color references are made to The Royal Horticultural Society Colour Chart (2001). Plants used for the description were grown for one year. Measurements and numerical values represent averages of typical plants.

Botanical classification: *Sedum sexangulare* cultivar Yellowstone.

Parentage: An open pollinated seedling of *Sedum sexangulare* 'Golddigger'.

Propagation: Vegetative division and cutting propagation.

Plant description: Typical and observed plant habit of the new *Sedum sexangulare* is basal clumps, reaching 30 cm wide with upright 10-11 cm tall stems topped by yellow flowers in July.

*Plant height*.—Average 10-11 cm.
*Plant width*.—33 cm.
*Stem color*.—144 C in spring, summer, and fall.
*Stem shape*.—Both typical and observed — round.
*Stem texture*.—Glabrous.
*Stem length*.—10 cm.
*Stem diameter*.—1-2 mm.
*Lateral branches*.—3-5 cm.
*Internode length*.—1-2 cm.

Foliage:

*Type*.—Semi-evergreen.
*Shape*.—Acicular.
*Petiole*.—None.
*Length*.—8 mm.
*Width*.—1 mm.
*Thickness*.—1-2 mm.
*Margin*.—Entire.
*Leaf apex, typical and observed*.—Acute.
*Leaf bases, typical and observed*.—Sessile.
*Texture*.—Smooth.
*Leaf arrangement*.—Whorled, crowded except at the base of the stems.
*Leaf venation pattern*.—None noticed.
*Leaf vein color*.—None noticed.
*Adaxial leaf description*.—Color is 144 A and B in late summer to winter and 1 A and B in spring.
*Abaxial leaf description*.—Color is 144 A and B in late summer to winter and 1 A and B in spring.
*Fall foliage color*.—None noticed.

Flower:

*Petal count*.—5.
*Petal shape*.—Lanceolate.
*Adaxial petal color*.—12 A.
*Abaxial petal color*.—12 A.
*Petal apex shape*.—Acuminate.
*Petal base*.—2 mm wide.
*Petal length*.—5 mm.
*Petal width*.—2 mm.
*Petal texture*.—Typical and observed — glabrous.
*Petal margin, typical and observed*.—Entire.
*Petal bases, typical and observed*.—Obovate.
*Inflorescence type*.—Panicle on basal flowering stems.
*Panicle color*.—12 A.
*Individual flower size*.—12 mm diameter, 5-6 mm depth.
*Flower shape*.—Stellate.
*Inflorescence length*.—5-6 cm and width — 6 cm across, 2 cm tall.
*Flower number*.—Approximately 35 per stem, 1400 plus per plant.
*Bloom period and duration*.—Mid-June to Mid-July.
*Flower longevity and duration on the plant*.—Approximately 3 weeks.
*Bud shape, typical and observed*.—Aristate.
*Bud length, typical and observed*.—6 mm.
*Bud diameter, typical and observed*.—2 mm.
*Bud color, typical and observed*.—Close to 1 A and B.
*Sepal size*.—Less than 1 mm across, 2 mm length.
*Sepal number*.—5.
*Sepal shape, typical and observed*.—Lanceolate.
*Sepal apex, typical and observed*.—Acute.
*Sepal margin, typical and observed*.—Entire.
*Sepal color, abaxial and adaxial typical and observed*.—Close to 151 B.
*Peduncle length, typical and observed*.—10 cm.
*Peduncle diameter, typical and observed*.—2-3 mm.
*Peduncle color, typical and observed*.—Close to 1 B and C.
*Peduncle texture, typical and observed*.—Glabrous.
*Pedicel length, typical and observed*.—3 mm.
*Pedicel diameter, typical and observed*.—1 mm or less.
*Pedicel color, typical and observed*.—Close to 1 B and C.
*Pedicel texture, typical and observed*.—Glabrous.
*Carpel color*.—1 A.
*Carpel surfaces*.—Glabrous.
*Stigma shape*.—Capitate.
*Stigma size*.—1 mm.
*Stigma color*.—1 A.
*Style length*.—1-2 mm.
*Style shape*.—Slender.
*Style color*.—1 A.
*Ovary size*.—1-2 mm.
*Ovary shape*.—Aristate.
*Ovary color*.—1 A.
*Pistil, typical and observed number*.—5, length 3-4 mm.
*Fertility*.—10 anthers, 10 stamens.
*Anther color*.—12 A, Pollen color — close to 17 B. Pollen amount — moderate.
*Anther shape*.—Elliptic, Anther length — almost 1 mm, Anther length — 1 mm.
*Filament color*.—12 A.
*Blooming habit*.—Terminal panicle on up to 10 cm stems.
*Scent*.—No scent noticed.
*Fruit*.—None.
*Hardiness*.—U.S.D.A. hardiness zones 4-9.
*Disease resistance*.—Resistance to diseases common to *Sedum* has not been observed on plants grown under nursery conditions.
*Pest resistance*.—Resistance to pests common to *Sedum* has not been observed on plants grown under nursery conditions.

I claim:

1. A new, distinct *Sedum sexangulare* plant as illustrated and described, characterized by larger foliage and golden yellow foliage color in early summer, compared to the smaller chartreuse foliage in early summer of the parent plant.

* * * * *